United States Patent [19]

Muto et al.

[11] Patent Number: 5,185,481
[45] Date of Patent: Feb. 9, 1993

[54] METHOD FOR THE SEPARATION OF IMPURITIES FROM CRUDE ETHANOL AQUEOUS SOLUTION

[75] Inventors: Tsunehisa Muto; Futoshi Kanegae, both of Tokuyama; Toru Takatsuka, Yokohama; Seiya Hirohama, Yokohama; Masazumi Ojiro, Yokohama, all of Japan

[73] Assignee: Japan as represented by Ministry of International Trade and Industry, Director-General, Tokyo, Japan

[21] Appl. No.: 776,275
[22] PCT Filed: Mar. 8, 1991
[86] PCT No.: PCT/JP91/00321
 § 371 Date: Nov. 26, 1991
 § 102(e) Date: Nov. 26, 1991
[87] PCT Pub. No.: WO91/16288
 PCT Pub. Date: Oct. 31, 1991

[30] Foreign Application Priority Data

Apr. 16, 1990 [JP] Japan .................................... 2-97535

[51] Int. Cl.$^5$ ........................ C07C 29/86; C07C 31/08
[52] U.S. Cl. ..................................................... 568/918
[58] Field of Search ......................................... 568/918

[56] References Cited

U.S. PATENT DOCUMENTS 4,769,112 9/1988 Wheldon .............. 203/119
4,842,693 6/1989 Wheldon .............. 202/154

FOREIGN PATENT DOCUMENTS 077745 8/1984 European Pat. Off. .
129459 12/1984 European Pat. Off. ............ 568/918
60-41627 3/1985 Japan .
62-29988 2/1987 Japan .
62-223138 10/1987 Japan .
2049741 2/1990 Japan .

OTHER PUBLICATIONS

De Filippi et al., Biotechnol. Bioeng. Symp. Dec. 1982, (Symp. Biotechnol. Energy Prod. Conserv. 4th) pp. 205–219.
Chemical Abstracts, 98 (14) 109269v (1983) *abstract*.

Primary Examiner—Joseph E. Evans
Attorney, Agent, or Firm—Browdy and Neimark

[57] ABSTRACT

The present invention is a method for the separation of impurities from a crude ethanol aqueous solution, comprising of; (i) extracting lipophilic impurities within the crude ethanol aqueous solution into an extracting solvent phase by treating the crude ethanol aqueous solution with an extracting solvent comprising carbon dioxide in a liquid state or carbon dioxide in a super-critical state under conditions wherein a ratio of the weight of the extracting solvent to the weight of the crude ethanol aqueous solution is 2 or higher; and (ii) recovering ethanol entrained with the extracting solvent or ethanol and methanol entrained with the extracting solvent into an aqueous phase by contacting the extracting solvent phase resulting after extracting the impurities to with water in a countercurrent manner under pressures in a ratio of the weight of water to the weight of the extracting solvent of 0.3 or lower. In this method for separation, the extracting solvent ratio by weight in the step of extracting impurities is preferably 6 or higher when the crude ethanol is fermented ethanol and the extracting solvent ratio by weight therein is preferably 3 or higher when the crude ethanol is synthesized ethanol. The aqueous phase obtained in the step (ii) of washing with water is recirculated to the step (i) of extracting impurities.

The method according to the present invention can yield a highly pure ethanol aqueous solution with high efficiency.

7 Claims, 1 Drawing Sheet

METHOD FOR THE SEPARATION OF IMPURITIES FROM CRUDE ETHANOL AQUEOUS SOLUTION

DESCRIPTION

1. Technical Field

The present invention relates to a method for the separation of impurities from a crude ethanol aqueous solution and, more particularly, to a method for removing impurities from an ethanol aqueous solution producible, for example, by fermentation.

2. Background Art

Ethanol is producible by fermentation of sugars such as molasses and so on or by hydration of ethylene (the two methods may hereinafter be referred to as fermentation method or synthesis method, respectively). Ethanol producible from the fermentation method and synthesis method is a crude ethanol aqueous solution in which a variety of impurities is contaminated. Main impurities contained in the crude ethanol aqueous solution obtainable by the fermentation method include methanol, acetaldehyde, n-propanol, n-butanol, ethyl acetate, 3-methylbutanol, and so on, and a large number of impurities is contained therein.

On the other hand, main impurities contained in the crude ethanol aqueous solution obtainable by the synthesis method include acetaldehyde, diethyl ether, acetone, secondary butanol, n-butanol, crotonaldehyde, etc. Likewise, this crude ethanol aqueous solution contains many kinds of impurities.

The impurities contained in the crude ethanol aqueous solution is so large in number of kinds, as described hereinabove, and so small in quantity that it is very difficult to remove them.

The crude ethanol aqueous solution containing such a large number of the impurities as described hereinabove is generally purified by distillation method.

This treatment uses a number of distillation towers and consumes a large quantity of steam for distillation. At least one of the distillation towers is operated by extraction and distillation system, in which a large quantity of water is added again to ethanol which has once been distilled and concentrated and the resulting mixture is then fed to the other distillation tower for treatment. Hence, conventional method for the purification of ethanol is extremely poor in energy efficiency.

In order to improve the problem with energy efficiency as recognized for the distillation method as described hereinabove, Japanese Patent Laid-open Publication (kokai) No. 41,627/1985 proposes the method for purifying crude ethanol by using carbon dioxide in a liquid state or in a supercritical state.

This method adopts processes removing carbon dioxide and diluting with water for recovering ethanol entrained in the carbon dioxide gases, together with impurities. This method, however, requires operation of separating an organic phase from an aqueous phase and operation of elevating pressures for recirculation of the aqueous solution. Further, this method is found insufficient in the recovery of ethanol.

On the other hand, the present inventors have proposed a method for purification and concentration by carrying out two-step extraction of a crude ethanol aqueous solution producible by the fermentation method with carbon dioxide in a liquid state or in a supercritical state, as disclosed in Japanese Patent Application No. 199,800/1988. This method, however, does not yet reach a sufficient level of purification.

The object of the present invention is to provide an efficient method for the purification of ethanol, which can solve the defects as seen in the conventional technology.

DISCLOSURE OF INVENTION

It is known that, when a crude ethanol aqueous solution is extracted with carbon dioxide in a liquid state under high pressures or with carbon dioxide in a supercritical state, a rate at which lipophilic impurities in the crude ethanol aqueous solution are extracted increases as a ratio of the weight of an extracting solvent (i.e. a ratio of the weight of the extracting solvent to the weight of a crude ethanol aqueous solution; this ratio may hereinafter be referred to as merely an extracting solvent ratio) increases, and a substantially entire quantity of the lipophilic impuritiesis extracted and transferred to an extract phase, when the extracting agent ratio is larger than a certain value. The term "lipophilic impurities" referred to herein is intended to mean an alcohol having three carbon atoms or more and an oxygenous compound having oxygen and having two carbon atoms or more, mainly a C3-C5 alcohol and a C2-C4 oxygenous compound, respectively. It is noted that the impurities contained in the crude ethanol aqueous solution obtainable from the synthesis method are composed of lipophilic impurities only, while the impurities contained in the crude ethanol aqueous solution obtainable from the fermentation method are composed of methanol as a hydrophilic impurity as well as the lipophilic impurities.

On the other hand, a raffinate phase contains ethanol alone when the crude ethanol aqueous solution obtainable from the synthesis method is treated with extraction, while both ethanol and methanol alone are left when the crude ethanol aqueous solution obtainable from the fermentation method is treated with extraction.

However when the crude ethanol aqueous solution obtained by the synthesis method is extracted at an increased extracting solvent ratio, a quantity of ethanol transferred to an extract phase is increased to a great amount so that the lipophilic impurities can be separated if the ethanol could be recovered from the extract phase with high efficiency.

Further, when the crude ethanol aqueous solution obtained by the fermentation method is extracted at a high extracting solvent ratio, quantities of both of ethanol and methanol, in addition to lipophilic impurities, are increased in the extract phase, too, so that the lipophilic impurities can be separated if ethanol alone or both of ethanol and methanol could be recovered from the extract.

As a result of extensive research on processes for such recovery, it has been found that the object of the present invention can be achieved by extracting the extract phase with water. The present invention has been completed by this finding.

More specifically, the present invention provides the method for the separation of impurities from a crude ethanol aqueous solution, comprising of:

(i) extracting lipophilic impurities within the crude ethanol aqueous solution into an extracting solvent phase by treating the crude ethanol aqueous solution with an extracting agent comprising carbon dioxide in a liquid state or carbon dioxide in a supercritical state under conditions wherein a extracting solvent ratio (a ratio of the weight of the extracting solvent to the weight of the crude ethanol aqueous solution) is 2 or higher; and (ii) recovering ethanol entrained with the extracting solvent or ethanol and methanol entrained with the extracting solvent into an aqueous phase by contacting the extracting solvent phase resulting after extracting the impurities with water in a countercurrent contact manner under pressures in a ratio of the weight of water to the weight of the extracting solvent phase (a water to extracting solvent ratio by weight) of 0.3 or lower.

Also, the present invention provides the method for the separation of impurities from the crude ethanol aqueous solution, wherein the extracting solvent ratio by weight in the step of extracting the impurities is 6 or higher when the crude ethanol aqueous solution is ethanol produced by the fermentation method or the extracting solvent ratio by weight therein is 3 or higher when the crude ethanol aqueous solution is ethanol produced by the synthesis method.

Furthermore, the present invention provides the method for the separation of impurities from the crude ethanol aqueous solution, wherein the aqueous phase obtained in the step (ii) of washing with water is recirculated into the step (i) of extracting the impurities.

BEST MODE FOR CARRYING OUT THE INVENTION

Figure 1:
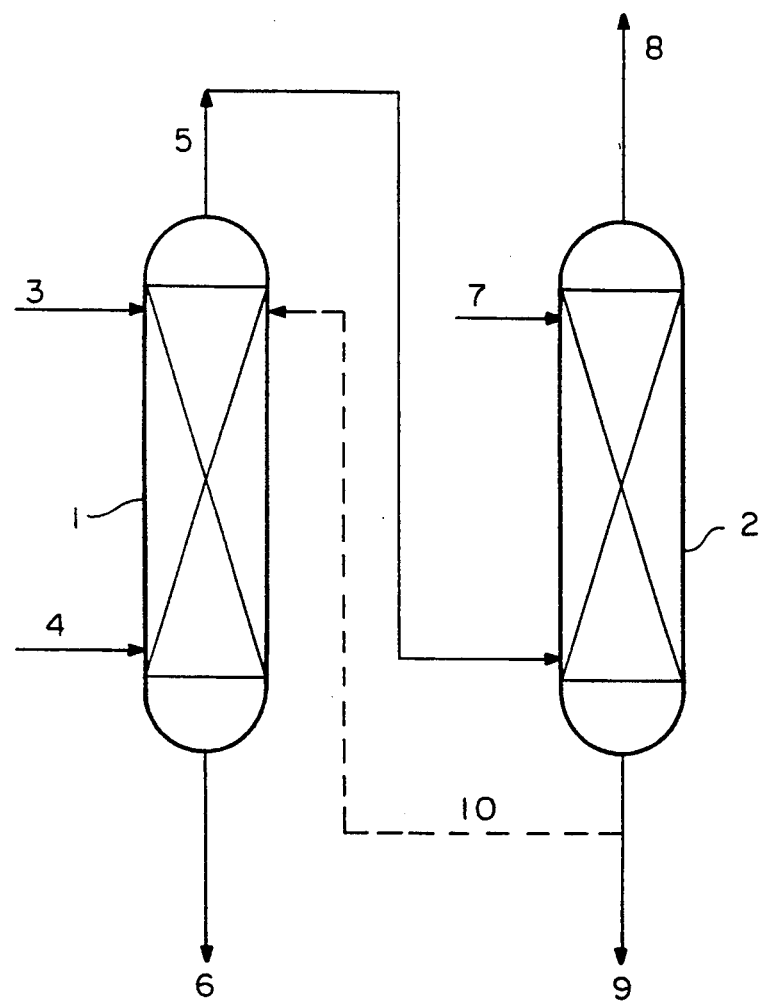
FIG. 1 is a flow sheet of the processes according to the present invention.

The crude ethanol aqueous solution to be employed as a raw material for the present invention may be prepared by the fermentation method or the synthesis method.

The concentration of ethanol in the crude ethanol aqueous solution may range generally from 5% to 40% by weight, specifically from 10% to 15% by weight for the crude ethanol aqueous solution produced by the fermentation method and from 15% to 20% by weight for the crude ethanol aqueous solution produced by the synthesis method.

The extracting solvent to be employed for the present invention may include carbon dioxide in a liquid state under high pressures or carbon dioxide in a supercritical state. For the present invention, there may be preferably employed carbon dioxide under pressure ranging from 40 k//cm$^2$ to 150 kg/cm$^2$ and at temperature ranging from 20° C. to 60° C. It is noted that the pressure referred to in this description is intended to mean a gauge pressure.

For the extracting agent, it is found that, as the quantity of the extracting solvent increases, lipophilic impurities in the crude ethanol aqueous solution are transferred into the extract phase to a larger amount and that they are transferred into the extract phase at the rate of almost 100% when the extracting solvent ratio has reached a certain ratio. However, as the concentration of impurities in the crude ethanol aqueous solution may vary to a considerable extent with conditions of preparation and the kind of raw materials, etc. so that a minimum of the extracting solvent ratio may vary accordingly. Hence, as illustrated in working examples as will be described hereinafter, as a result of experiment in which representative components of impurities are added to a pure ethanol aqueous solution at a rate larger than a normal concentration of a raw material, it has been found that the extracting solvent ratio for efficient extraction is 8 or higher, more specifically within the range from 8 to 18, for ethanol produced by the fermentation method, while the extracting solvent ratio for efficient extraction is 5 or higher, more specifically within the range from 5 to 12, for ethanol produced by the synthesis method. Although the present invention can be performed in a ratio over the maximum extracting solvent ratio as described hereinabove, economical benefits can be less achieved to such an extent as commensurate with the ratio exceeding the maximum ratio.

In the specifications for industrial hydrous alcohol, etc., a tolerance limits of concentrations is set for each of impurities. As it is considered that 100% of the impurities should not necessarily be removed for practical application when concentrations of the impurities are low in the raw materials, an extracting solvent ratio for practical extraction may be as sufficient as from 2 or higher, more specifically in the range from 2 to 12. Particularly, for ethanol produced by the fermentation method, the extracting agent ratio may range from 6 to 12. For ethanol produced by the synthesis method, the extracting solvent ratio may preferably be 3 or higher, specifically in the range from 3 to 8. It is to be noted herein that the maximum value of the extracting solvent ratio is a value determined from an economical point of view.

When the crude ethanol aqueous solution produced by the synthesis method is extracted in the extracting solvent ratio ranging from 5 to 12, a total quantity of the lipophilic impurities and 35% of ethanol or more in the raw materials are transferred into the extract phase, while ethanol alone is left in the raffinate phase.

On the other hand, when the crude ethanol aqueous solution produced by the fermentation method is extracted in the extracting solvent ratio ranging from 8 to 18, a total amount of the lipophilic impurities, 55% of ethanol or more and 20% of methanol or more in the raw materials are transferred into the extract phase, while ethanol and methanol alone are left in the raffinate phase.

In either case, the extract phase is introduced under pressures into an extraction tower for washing with water, thereby allowing it to be contacted with water added from outside in a countercurrent manner.

When ethanol containing a large quantity of lipophilic impurities is washed merely with water, acetone and so on are caused to become an aqueous solution and cannot be separated, although a portion of butanol etc. can be separated. Surprisingly, however, it has been found that transferal of the lipophilic impurities into the aqueous phase is decreased usually at the ratio by weight of the water to extracting solvent (water-to-extract ratio) of 0.3 or smaller, when the extract phase, in which ethanol and the lipophilic impurities are dissolved in the carbon dioxide in a liquid state under high pressures, or carbon dioxide in a supercritical state or the extract, in which ethanol, methanol and the lipophilic impurities are dissolved in the carbon dioxide in a liquid state under high pressures or carbon dioxide in a supercritical state, is contacted with water in a countercurrent manner. For instance, it has been found that transferal of acetone into the aqueous phase is reduced to a level as low as 12% or smaller in the water-to-extract ratio ranging from 0.02 to 0.1.

Further, it is noted that quantities of components to be transferred into the aqueous phase within the aforesaid range may vary to a great amount according to kind of components, and methanol and ethanol are likely to be transferred most. It is further noted that the quantities of ethanol and methanol vary to a great extent With the water-to-extract ratio. Specifically, ethanol may be transferred in the rate of 25% to 30% at the water to extract ratio of 0.02. This quantity may increase in proportion to an increase in the quantity of water, and 90% of ethanol is transferred into the aqueous phase in the water-to-extractation of 0.08, while an almost entire quantity of ethanol is transferred into the aqueous phase in the water-to-extract ratio of 0.1.

On the other hand, the quantity of the lipophilic impurities to be transferred into the aqueous phase is smaller than those of ethanol and methanol and 10% of the lipophilic impurities or less can be transferred thereinto in the water-to-extract ratio ranging from 0.02 to 0.1. Propyl alcohol and acetaldehyde may be transferred into the aqueous phase in somewhat larger quantities as well as 10% to 50% of propyl alcohol and 5% to 25% of acetaldehyde are transferred thereinto at the water-to-extract ratio ranging from 0.02 to 0.1.

A novel purification method as will be described hereinafter has been devised on the basis of the aforesaid finding.

More specifically, when the operation is carried out by comparing the concentrations of the lipophilic impurities within the raw materials with the acceptable scope of the concentrations of the lipophilic impurities in purified products and by appropriately selecting the extracting agent ratio in the extraction of impurities and the water-to-extract ratio by weight in the extraction by washing with water, an ethanol aqueous solution or an ethanol-methanol aqueous solution, each being purified to such an amount as containing negligible small quantity of lipophilic impurities, can be produced. A combined yield of purified ethanol by extracting the impurities and by extracting via washing with water is in the range of 97% to 98%, for example, when the extracting solvent ratio is set to 6 and the water-to-extract ratio by weight is set to 0.08, while a combined yield of purified ethanol may range from 90% to 91% when the extracting solvent ratio is set to 8 and the water-to-extract ratio by weight is set to 0.06. Such yields are extremely high and mean that in fact 90% of the total quantity of the each lipophilic impurities has been removed. Further, in some cases, the extracting solvent ratio in the extraction of the impurities may be reduced to an extent lower than the aforesaid level, thereby leaving approximately 10% of the lipophilic impurities and thereafter increasing the water-to-extract ratio by weight in the extraction by washing with water.

The present invention will be described with reference to the accompanying drawing.

FIG. 1 is a flow sheet according to the present invention.

As shown in FIG. 1, the crude ethanol aqueous solution containing ethanol and impurities is introduced into an upper portion of a tower 1 for extracting impurities through a line 3, while the extracting solvent consisting of carbon dioxide is introduced into a lower portion of the tower 1 for extracting the impurities through a line 4.

In the tower 1 for extracting the impurities, the crude ethanol aqueous solution is allowed to be contacted with the extracting solvent in a countercurrent fashion.

The ratio by weight of the extracting solvent to the crude ethanol aqueous solution (the ratio of the weight of the extracting solvent to the weight of the crude ethanol aqueous solution) in the tower 1 for extracting the impurities may usually be 2 or higher, preferably from 6 to 12 for the crude ethanol aqueous solution producible by the fermentation method and from 3 to 8 for the crude ethanol aqueous solution producible by the synthesis method. Under these conditions, the lipophilic impurities in the impurities which are contained in the crude ethanol aqueous solution are transferred to the extracting agent e, thereby yielding an extract phase containing .of those lipophilic substances, water and ethanol (additionally containing a small quantity of methanol for the crude ethanol aqueous solution producible by the fermentation method). The resulting extract phase is then introduced under pressures into a lower portion of a tower 2 for washing with water through a line 5.

Introduced into an upper portion of the tower 2 for extraction by washing with water is water under pressure (specifically from 40 kg/cm$^2$ to 150 kg/cm$^2$) at temperature (specifically from 20° C. to 60° C.) substantially equal to the pressure and the temperature of the extract phase, respectively, through a line 7. In the tower 2 for washing with water, the extract phase is allowed to be contacted with the water in a countercurrent manner.

The water-to-extract ratio, namely the ratio of water to the extract phase by weight is usually 0.3 or lower, particularly in the range from 0.02 to 0.1. Under these circumstances, the ethanol in the extract phase as well as ethanol and methanol in the extract phase, when methanol is contained, are transferred to the aqueous phase in a large quantity and stay on a bottom of the tower 2 for washing. It is to be noted herein that the quantity of the lipophilic impurities to be transferred to the aqueous phase is 10% or less as a whole.

On the other hand, a raffinate phase consisting of water and ethanol, or consisting of water, ethanol and methanol when the crude ethanol aqueous solution contains methanol, is held in a bottom portion of the tower 1 for extracting impurities. In other words, the raffinate phase and the aqueous phase consist of a pure ethanol aqueous solution or a pure alcohol solution composed of pure ethanol and pure methanol, each containing substantially no lipophilic impurities, so that they may be concentrated or concentrated and subjected to removal of methanol, in order to meet purposes. The raffinate phase in the tower for extracting impurities is withdrawn through a line 6, while the aqueous phase in the tower 2 for washing with water is withdrawn through a line 9. After degassed, the raffinate phase and the aqueous phase are then fed to a variety of known devices for concentrating ethanol or to a device for concentrating ethanol and removing methanol.

Also, the aqueous phase in the tower 2 for washing with water may be recirculated to a top portion of the tower 1 for extracting the impurities through a line 10 without being withdrawn through the line 9. In this case, it is advantageous that a rate of removal of the lipophilic impurities is further improved.

In this method, the concentration of ethanol in the liquid raw material to be fed to the tower 1 for extracting impurities may usually range from 5% to 40% by weight. The conditions under which the tower 1 for extracting impurities and the tower 2 for washing with water are operated are such that the temperature ranges 20° C. to 60° C. and the pressure ranges from 40 kg/cm² to 150 kg/cm².

As the tower for extracting impurities and the tower for washing with water, there may be employed conventionally known device with a contacting mechanism such as a filler, a grating plate, a rotary disk plate, shelf boards, etc. built therein.

EXAMPLES

The present invention will be described more in detail by way of examples.

EXAMPLE 1

1-1. By using a tower for extracting impurities, 25 mm in inner diameter and 3 m in height, with 30 baffle trays built therein a sample similar to a crude ethanol aqueous solution producible by the fermentation method yet containing a somewhat larger quantity of impurities was extracted. As a crude ethanol aqueous solution, there was employed the said sample of a solution which was prepared by adding 0.2% by weight of each of methanol, n-propanol, ethyl acetate, acetaldehyde and 3-methylbutanol to an ethanol aqueous solution containing ethanol in the concentration of 10% by weight.

Said sample of the solution was fed at the rate of 500 grams per hour from the top of the tower for extracting impurities. An extracting agent consisting of carbon dioxide in a liquid state was fed from a bottom portion of the tower so as to give a predetermined ratio by weight of the extracting solvent to the aqueous solution (namely the extracting solvent ratio and a G/L ratio in table The pressure within the tower was held at 100 kg/cm² and the temperature in the tower as a whole was as high as 40° C.

In order to analyze the components contained in the extract phase, the extract was withdrawn from the top portion of the tower and treated under reduced pressures to vaporize the extracting solvent alone, thereby yielding an ethanol aqueous solution. On the other hand, the raffinate phase was withdrawn from the bottom portion of the tower and treated under reduced pressures, thereby vaporizing the extracting solvent only and leaving an ethanol aqueous solution.

Table 1 shows rates of extraction of components obtained from the extract phase in the experiments operated as described hereinabove.

TABLE 1

| G/L (wt/wt) | 2.00 | 4.00 | 6.00 | 8.00 | 10.00 |
|---|---|---|---|---|---|
| EtOH (ethanol) | 14.0 | 28.0 | 41.9 | 55.9 | 69.1 |
| MeOH (methanol) | 6.2 | 12.4 | 18.6 | 24.8 | 31.0 |
| PrOH (propanol) | 37.2 | 72.8 | 91.9 | 97.0 | 98.5 |
| i-AmOH (isoamyl-alcohol) | 99.5 | 99.8 | 99.8 | 99.9 | 99.9 |
| Ac-CHO (acetaldehyde) | 95.6 | 99.4 | 99.9 | 99.8 | 99.8 |
| Ac-Et (ethyl acetate) | 99.8 | 99.9 | 99.9 | 99.9 | 99.9 |

1.2 Then, ethanol was recovered from the extract phase obtained in process 1.1 above by using a tower for washing with water, 3.8 mm in inner diameter and 3 m in height, with Raschig rings filled therein. In this case, the extract phase obtained in the process 1.1 above was fed from the bottom of the tower for washing with water at the rate of 1,200 grams per hour while washing water was fed from the top of the tower so as to give a predetermined ratio of washing water to extracting solvent (namely water-to-extract ratio and W/G in Table). The tower was held under inner pressure of 100 kg/cm² and at temperature of 40° C. as a whole. The extract phase was withdrawn from the top of the tower and continuously treated to vaporize the extracting solvent alone, thereby collecting the lipophilic impurities. On the other hand, the raffinate phase was withdrawn from the bottom of the tower and treated under reduced pressures, thereby vaporizing the extracting solvent alone and yielding an ethanol aqueous solution. Table 2 below shows rates of extraction of components by washing with water in the extraction experiments operated in the manner as described hereinabove.

The rate by washing with water was calculated as follows:

$$\text{Rate by washing with water} = \frac{\text{Quantity of Component Obtainable from Raffinate phase}}{\text{Quantity of Component Supplied from Extract phase}}$$

Table 3 below shows combined rates of recovery of ethanol from the raffinate phase obtained by extracting the impurities and from the aqueous phase obtained by washing with water.

TABLE 2

| W/G (wt/wt) | 0.02 | 0.04 | 0.06 | 0.08 | 0.10 |
|---|---|---|---|---|---|
| EtOH | 28.5 | 56.8 | 82.0 | 96.2 | 99.5 |
| MeOH | 63.8 | 98.7 | 99.9 | 100.0 | 100.0 |
| PrOH | 10.7 | 21.4 | 32.2 | 42.9 | 53.5 |
| i-AmOH | 1.3 | 2.7 | 4.0 | 5.4 | 6.8 |
| Ac-CHO | 3.0 | 6.0 | 9.0 | 12.0 | 15.0 |
| Ac-Et | 0.4 | 0.9 | 1.4 | 1.9 | 2.3 |

TABLE 3

(Rates of Recovery of Ethanol by Towers for Extraction of Impurities + Washing with Water)

| (W/G) → <br> (G/L) ↓ | 0.06 | 0.08 | 0.10 |
|---|---|---|---|
| 6.0 | 88.5 | 97.3 | 99.6 |
| 8.0 | 81.4 | 95.4 | 99.4 |
| 10.0 | 71.3 | 92.2 | 98.9 |

EXAMPLE 2

2-1. Procedures were followed in substantially the same manner as in process 1.1 of Example 1 above, except for using a sample similar to a crude ethanol aqueous solution obtainable by the synthesis method yet containing a somewhat larger quantity of impurities. The sample was prepared by adding 0.2% by weight of acetaldehyde, ethyl ether, acetone, methyl ethyl ketone and sec-butanol to an ethanol aqueous solution containing ethanol in the concentration of 20% by weight.

Table 4 below shows the rates of extraction of the components obtained from the extract phase in the extraction experiments operated in the manner as described hereinabove.

TABLE 4

| G/L (wt/wt) | 2.00 | 3.00 | 4.00 | 5.00 | 6.00 |
|---|---|---|---|---|---|
| EtOH (ethanol) | 15.4 | 23.1 | 30.8 | 38.5 | 46.1 |
| Ac-CHO (acetaldehyde) | 74.9 | 92.8 | 97.3 | 98.6 | 99.1 |
| Et-Ether (ethyl ether) | 99.8 | 99.9 | 99.9 | 99.9 | 99.9 |
| Acetone | 98.0 | 99.3 | 99.6 | 99.7 | 99.8 |
| MEK (methyl ethyl ketone) | 99.5 | 99.7 | 99.8 | 99.8 | 99.8 |
| s-BuOH (sec- | | 99.3 | 99.6 | 99.7 | 99.8 |

TABLE 4-continued butanol)

2-2. Ethanol was recovered from the extract phase obtained in the process 2-1 above in the same manner as in the process 1-2 above.

Table 5 shows rates of extraction of the components by washing with water in this example.

The rates by washing with water were determined in the same manner as described hereinabove.

Table 6 below shows combined rates of recovery of ethanol from the raffinate phase obtained by extracting the impurities and from the equeous phase obtained by washing with water.

TABLE 5

| W/G (wt/wt) | 0.02 | 0.04 | 0.06 | 0.08 | 0.10 |
|---|---|---|---|---|---|
| EtOH | 25.9 | 51.7 | 75.8 | 92.7 | 98.7 |
| Ac-CHO | 5.1 | 10.3 | 15.5 | 20.7 | 25.9 |
| Et-Ether | 0.4 | 0.8 | 1.2 | 1.7 | 2.1 |
| Acetone | 2.3 | 4.7 | 7.0 | 9.4 | 11.8 |
| MEK | 1.2 | 2.5 | 3.8 | 5.1 | 6.4 |
| s-BuOH | 1.6 | 3.2 | 4.8 | 6.5 | 8.1 |

TABLE 6

(Rates of Recovery of Ethanol by Towers for Extraction of Impurities + Washing with Water)

| (W/G) → <br> (G/L ↓ | 0.06 | 0.08 | 0.10 |
|---|---|---|---|
| 4.0 | 90.3 | 96.9 | 99.4 |
| 5.0 | 86.8 | 95.6 | 99.2 |
| 6.0 | 82.8 | 94.1 | 98.9 |

INDUSTRIAL APPLICABILITY

The purified ethanol aqueous solution obtainable by the present invention is a solution of high purity, which does not contain a substantial quantity of impurities. Such a purified ethanol aqueous solution may be converted into anhydrous ethanol or a hydrous ethanol containing ethanol in the concentration 95% by volume or higher by subjecting it to distillation in conventional manner or by subjecting it to adsorption treatment.

The method according to the present invention is a method efficient in energy and advantageous because it is based primarily on extraction treatment so that it has a great industrial significance.

We claim:

1. A method for the separation of impurities from a crude ethanol aqueous solution, comprising of:
   (i) extracting lipophilic impurities within the crude ethanol aqueous solution into an extracting solvent phase by treating the crude ethanol aqueous solution with an extracting solvent comprising carbon dioxide in a liquid state or carbon dioxide in a supercritical state under conditions wherein a ratio of the weight of the extracting solvent to the weight of the crude ethanol aqueous solution (an extracting solvent to crude ethanol aqueous solution ratio by weight) is 2 or higher; and
   (ii) recovering ethanol entrained with the extracting solvent or ethanol and methanol entrained with the extracting solvent into an aqueous phase by contacting the extracting solvent phase resulting after extracting the impurities with water in a counter-current manner under pressures in a ratio of the weight of water to the weight of the extracting solvent phase (a water to extracting solvent ratio by weight) of 0.3 or lower.

2. A method for the separation of impurities from a crude ethanol aqueous solution as claimed in claim 1, wherein the extracting solvent ratio by weight in the step of extracting impurities is from 6 to 12 when the crude ethanol aqueous solution is produced by fermentation method and the extracting solvent ratio by weight is from 3 to 8 when the crude ethanol aqueous solution is produced by synthesis method.

3. A method for the separation of impurities from a crude ethanol aqueous solution as claimed in claim 1, wherein the extracting solvent ratio by weight in the step of extracting impurities is from 8 to 18 when the crude ethanol aqueous solution is produced by fermentation method and the extracting solvent ratio by weight therein is from 5 to 12 when the crude ethanol aqueous solution is produced by synthesis method.

4. A method for the separation of impurities from a crude ethanol aqueous solution as claimed in claim 1, wherein the aqueous phase obtainable in the step (ii) of washing with water is recirculated to the step (i) of extracting impurities.

5. A method for the separation of impurities from a crude ethanol aqueous solution as claimed in claim 1, wherein a concentration of ethanol in the crude ethanol aqueous solution ranges from 5% to 40% by weight.

6. A method for the separation of impurities from a crude ethanol aqueous solution as claimed in claim 1, wherein a concentration of ethanol in the crude ethanol aqueous solution producible by fermentation method ranges from 10% to 15% by weight and a concentration of ethanol in the crude ethanol aqueous solution producible by synthesis method ranges from 15% to 20% by weight.

7. A method for the separation of impurities from a crude ethanol aqueous solution as claimed in claim 1, wherein the carbon dioxide is under pressure ranging from 40 kg/cm$^2$ to 150 kg/cm$^2$ and at temperature ranging from 20° C. to 60° C.

* * * * *